United States Patent [19]

Goldberg et al.

[11] 4,176,186

[45] Nov. 27, 1979

[54] QUATERNARY DERIVATIVES OF NOROXYMORPHONE WHICH RELIEVE INTESTINAL IMMOBILITY

[75] Inventors: Leon I. Goldberg, Chicago, Ill.; Herbert Merz, Ingelheim am Rhein; Klaus Stockhaus, Bingen, both of Fed. Rep. of Germany

[73] Assignee: Boehringer Ingelheim GmbH, Ingelheim am Rhein, Fed. Rep. of Germany

[21] Appl. No.: 928,821

[22] Filed: Jul. 28, 1978

[51] Int. Cl.$^2$ .................. A61K 41/485; C07D 489/00
[52] U.S. Cl. ........................................ 424/260; 546/45
[58] Field of Search ..................... 260/285; 546/44, 45; 424/260

[56] References Cited

U.S. PATENT DOCUMENTS 3,101,339   8/1963   Zeile et al. .................... 260/285

OTHER PUBLICATIONS

Van Nueten, et al., Chemical Abstracts, vol. 81, 114464g (1974).
Ehrenpreis, et al., Chemical Abstracts, vol. 83, 126360z (1975).
Van Nueten, et al., Chemical Abstracts, vol. 85, 251n (1976).

*Primary Examiner*—Donald G. Daus
*Assistant Examiner*—Diana G. Rivers
*Attorney, Agent, or Firm*—Hammond & Littell

[57] ABSTRACT

Compounds of the formula

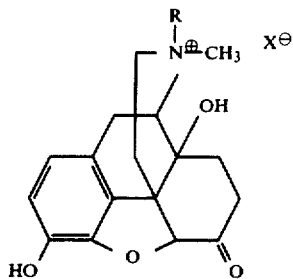

wherein
R is allyl or a related radical such as chloroallyl, cyclopropyl-methyl or propargyl, and
X is the anion of an acid, especially a chloride, bromide, iodide or methylsulfate anion;

the compounds prevent or relieve the intestinal mobility inhibiting side-effects of narcotic analgesics without interfering with the analgesic activity of the latter.

4 Claims, No Drawings

QUATERNARY DERIVATIVES OF NOROXYMORPHONE WHICH RELIEVE INTESTINAL IMMOBILITY

This invention relates to novel quaternary derivatives of noroxymorphone, and to methods of preparing and using these compounds.

More particularly, the present invention relates to a novel class of quaternary noroxymorphones represented by the formula

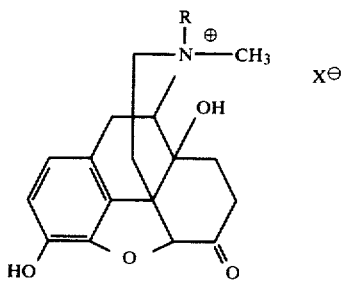

wherein
R is allyl, chloroallyl, cyclopropyl-methyl or propargyl, and
X is the anion of an acid, especially a chloride, bromide, iodide or methylsulfate anion.

The compound are referred to as N-substituted noroxymorphone methosalts.

The compounds embraced by formula I may be prepared by various methods involving known chemical synthesis principles, among which the following are preferred:

Method A

By quaternizing a tertiary N-substituted noroxymorphone of the formula

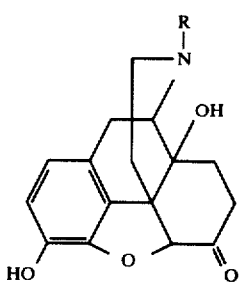

wherein R has the same meanings as in formula I, with a methylating agent of the formula $$CH_3-X \quad (III)$$

wherein X is chlorine, bromine, iodine or $-CH_3OSO_3$. For practical and economic reasons, methyl bromide, methyl iodide or dimethylsulfate are preferred as methylating agents.

At least equimolar amounts of II and III are required for complete conversion of II into I. However, with a view toward a smooth and rapid reaction, it is advantageous to provide the methylating agent III in excess, preferably in an amount of 3 to 10 mols per mol of compound II, and the excess methylating agent may simultaneously serve as the solvent medium for the reaction.

The reaction, may, however, also be preformed in another solvent medium, preferably in an inert solvent or mixture of inert solvents in which the starting compound II is sufficiently soluble, the rate of reaction is sufficiently rapid, and the formation of side-products is at a minimum. Examples of suitable such solvents are methanol, ethanol, or other alcohols, methylene chloride, chloroform, tetrahydrofuran, dioxane, dimethylformamide, dimethylsulfoxide, acetonitrile, nitromethane or hexamethylphosphoric triamide. Especially preferred is acetone from which the reaction product precipitates during the reaction in very pure crystalline form.

The reaction temperature can be varied within wide limits, but most advantageous is a temperature range in which, on the one hand, the reaction still proceeds sufficiently rapidly and, on the other hand, side reactions are not yet predominant. Reaction temperature between $-10°$ and $+150°$ C. are advantageous, and the range between $0°$ and $100°$ C. is preferred.

Method B

By quaternizing an O-substituted tertiary noroxymorphone of the formula

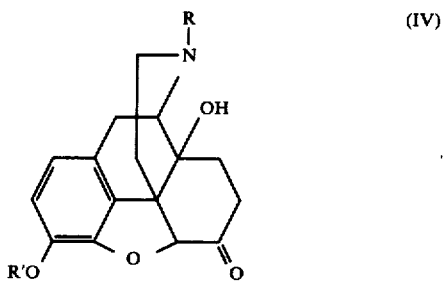

wherein
R has the same meanings as in formula I, and
R' is a substituent which can be introduced into compound II by known chemical methods and then removed again without altering the molecular structure, primarily methoxymethyl or acyl, especially acetyl, with a methylating agent of the formula III to form an O-substituted noroxymorphone methosalt of the formula

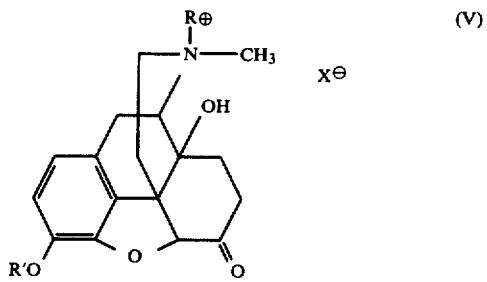

wherein R, R' and X have the meanings previously defined, and subsequently removing the substituent R' from the methosalt V by conventional methods, preferably by hydrolysis, to restore the phenolic hydroxyl group and form the desired end product of the formula I. This method has an advantage over method A in those cases where an undesirable O-methylation may take place besides the desired N-quaternization.

The quaternization of compound IV is carried out in analogy to and under the same reaction conditions as described in method A. It is particularly advantageous to perform method B as a continuous, single-step procedure, that is, without isolation of the intermediate V.

The end products of the formula I obtained by method A or B may be isolated from the reaction mixture and purified by conventional laboratory methods. If desired, a given anion in such an end product may be exchanged for another anion, which can also be done by conventional methods.

The starting compounds of the formula II are either known compounds or may be prepared by known methods, for instance by alkylation of noroxymorphone, as illustrated in Example 11(a) below.

Likewise, the starting compounds of the formula IV are either known or may be prepared by known methods, as illustrated in Example 9(a) below.

The following examples illustrate the present invention and will enable others skilled in the art to understand it more completely. It should be understood, however, that the invention is not limited solely to the particular examples given below.

EXAMPLE 1

N-Allyl-noroxymorphone methoiodide by method A

An excess of concentrated ammonia was added to a concentrated aqueous solution of 18.2 gm (0.05 mol) of N-allyl-noroxymorphone hydrochloride, whereupon the free base precipitated, which was separated by extraction with chloroform. The combined chloroform extracts were dried with sodium sulfate and evaporated in vacuo. The residue was dissolved in 150 ml of absolute acetone, the resulting solution was admixed with 18 ml (0.29 mol) of methyl iodide in a pressure vessel, the vessel was sealed, and the reaction mixture contained therein was heated at 70° C. for three days. Thereafter, the reaction product which had separated out in crystalline form was collected by suction filtration, washed first with absolute acetone and then with absolute ether, and dried at 80° C. 16.6 gm (70.5% of theory) of the compound of the formula

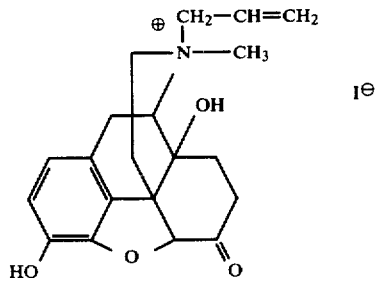

having a melting point of 217°–218° C. were obtained. Additional crystalline reaction product was obtained by evaporation of the mother liquor.

EXAMPLE 2

N-allyl-noroxymorphone methobromide by method A 36.4 gm (0.1 mol) of N-allyl-noroxymorphone hydrochloride were converted into the free base as described in Example 1. The free base was dissolved in 180 ml of absolute acetone, the solution was admixed with 33.0 ml (0.6 mol) of methyl bromide in a pressure vessel, the vessel was sealed, and its contents were heated at 70° C. for seven days. Thereafter, the reaction mixture was cooled, and the reaction product which had separated out in crystalline form was collected by suction filtration, washed first with a little absolute acetone and then with absolute ether, and dried at 80° C. 35 gm (85.5% of theory) of N-allyl-noroxymorphone methobromide, m.p. 246° C., were obtained. The melting point of a sample recrystallized from methanol remained unchanged at 246° C.

EXAMPLE 3

N-Allyl-noroxymorphone methomethylsulfate by method A 3.64 gm (0.01 mol) of N-allyl-noroxymorphone hydrochloride were converted into the free base, as described in Example 1. The free base was dissolved in 40 ml of absolute acetone, 3.8 gm (0.03 mol) of dimethyl sulfate were added to the solution, and the mixture was refluxed for 48 hours, during which time an oil gradually separated out. Thereafter, the oil was isolated by decanting the supernatent liquid, crystallized from methanol/ether, and the crystallizate was collected by suction filtration, washed first with absolute methanol/ether and then with absolute ether, and dried at 80° C. 0.9 gm of N-allyl-noroxymorphone methomethylsulfate, m.p. 219°–222° C., were obtained.

EXAMPLE 4

N-allyl-noroxymorphone methobromide by anion exchange 12.0 gm (0.0256 mol) of N-allyl-noroxymorphone methoiodide, prepared in accordance with Example 1, were dissolved in 500 ml of water, and the solution was filtered through a column charged with a strongly basic anion exchanger (bromide-loaded anion exchanger, 171 gm, with an exchange capacity of 0.513 Val). The column was subsequently rinsed with 1.5 liters of water, and the filtrates were combined and evaporated in vacuo at 70° C. The residue was dissolved in 100 ml of methanol, and 100 ml of ether were added to the solution, whereupon 9.65 gm (92% of theory) of the methobromide, m.p. 245° C., separated out. After recrystallization from methanol it had a melting point of 246° C.

EXAMPLE 5

N-Cyclopropylmethyl-noroxymorphone methobromide by method A 2.5 gm (7.35 millimols) of N-cyclopropylmethyl-noroxymorphone were dissolved in a mixture consisting of 50 ml of absolute acetone and 0.5 ml of dimethylformamide, and the resulting solution was admixed with 4.25 gm (44.8 millimols) of methyl bromide. The reaction mixture was then allowed to stand for three weeks at room temperature in a sealed pressure vessel. Thereafter, the contents of the vessel were evaporated, and the residue was crystallized from methanol and recrystallized from methanol/ether, yielding 1.0 gm of the methobromide which had a melting point of 253° C.

EXAMPLE 6

N-Cyclopropylmethyl-noroxymorphone methoiodide by method A 8.0 gm (0.0211 mol) of N-cyclopropylmethyl-noroxymorphone hydrochloride were converted into the free base, as described for N-allyl-noroxymorphone hydrochloride in Example 1. The free base was dissolved in 50 ml of absolute acetone in a pressure vessel, the solution was admixed with 8 ml (0.128 mol) of methyl iodide, the vessel was sealed, and the reaction mixture was heated at 70° C. for four days, during which time a viscous oil separated out. After cooling, the solvent was decanted, and the reside was crystallized from ethanol/ether, yielding 5.8 gm (57% of theory) of the methoiodide.

EXAMPLE 7

N-Cyclopropylmethyl-noroxymorphone methobromide by anion exchange 5.8 gm of N-cyclopropylmethyl-noroxymorphone methoiodide (see Example 6) were converted by anion exchange analogous to Example 4 into the methobromide 4.8 gm (94.7% of theory) of the methobromide, m.p. 253° C., were obtained. The melting point remained unchanged after recrystallization from methanol/ether.

EXAMPLE 8

N-Propargyl-noroxymorphone methobromide by method A 4.0 gm (12.29 millimols) of N-propargyl-noroxymorphone were dissolved in a mixture consisting of 30 ml of methanol and 20 ml of dimethylformamide, the solution was admixed with 6.8 gm (71.6 millimols) of methyl bromide, and the mixture was heated at 70° C. in a sealed pressure vessel for five days. Thereafter, the contents of the vessel were cooled and evaporated in vacuo. The residue was crystallized from ethanol/ether, recrystallized from water and dried at 80° C., yielding 1.1 gm (21.3% of theory) of the pure methobromide with a melting point of 220° C.

EXAMPLE 9

N-Allyl-noroxymorphone methobromide by method B (a) 10.9 gm (0.03 mol) of N-allyl-noroxoymorphone hydrochloride were converted into the free base, as described in Example 1. The evaporation residue of the combined chloroform extracts was dissolved in 70 ml of absolute methylene chloride, 3.4 gm (0.033 mol) of triethylamine were added and, while cooling the mixture on an ice bath, a solution of 2.6 gm (0.033 mol) of acetyl chloride in absolute methylene chloride was admixed therewith. The ice bath was then removed, and the reaction mixture was slowly allowed to warm to room temperature and was subsequently refluxed for one hour. Thereafter, the reaction solution was cooled, washed twice with ice water, dried with sodium sulfate and evaporated in vacuo, leaving as the residue O$^3$-acetyl-N-allyl-noroxymorphone.

(b) The evaporation residue obtained in step (a) was quaternized with methyl bromide in analogy to the procedure of Example 2. After a reaction time of seven days at 70° C., the reaction solution was evaporated in vacuo, leaving as the residue O$^3$-acetyl-N-allyl-noroxymorphone methobromide.

(c) The evaporation residue obtained in step (c) was dissolved in 1 N hydrobromic acid, and the solution was evaporated in vacuo on a water bath at 60° C. The residue was crystallized as described in Example 2, yielding 5.3 gm (41.7% of theory, based on the N-allyl-noroxymorphone hydrochloride starting material) of N-allyl-noroxymorphone methobromide, m.p. 247° C.

EXAMPLE 10

N-Allyl-noroxymorphone methobromide by method B 3.64 gm (0.01 mol) of N-allyl-noroxymorphone were converted into O$^3$-acetyl-N-allyl-noroxymorphone, as described in Example 9(a), and the evaporation residue was dissolved in 60 ml of absolute methylene chloride. While stirring and cooling it on an ice bath, the resulting solution was admixed with 2.22 gm (0.015 mol) of trimethyloxonium fluoroborate. After 1 hour the ice bath was removed, and the mixture was stirred for sixteen hours at room temperature. Thereafter, the reaction solution was evaporated, the residual quaternary fluoroborate was dissolved in 150 ml of water, and the solution was filtered, in analogy to Example 2, through a strong basic anion exchange column (175 gm, OH-form, about 0.25 Val), and the column was rinsed with about 1 liter of water. The combined aqueous solutions were then acidified with concentrated hydrobrmic acid (pH about 3) and subsequently evaporated in vacuo on a water bath at 60° C. The residue was crystallized from 75 ml of methanol and 30 ml of ether, yielding 1.5 gm (36.7% of theory) of N-allyl-noroxymorphone methobromide having a melting point of 246°-247° C. An additional amount of the methobromide was recovered from the mother liquor.

EXAMPLE 11

N-(Trans-3-chloroallyl)-noroxymorphone methobromide by method B (a) A mixture consisting of 6.48 gm (0.02 mol) of noroxymorphone hydrochloride, 4.2 gm of sodium bicarbonate, 2.44 gm (0.022 mol) of trans-3-chloroallyl chloride and 70 ml of dimethylformamide was stirred for four hours at 90° C. Thereafter, the reaction solution was evaporated in vacuo, and the residue was shaken with a mixture of 75 ml of chloroform and 75 ml of water. The chloroform phase was separated, and the aqueous phase was again extracted with 25 ml of chloroform. The combined chloroform extracts were washed with 50 ml of water, dried with sodium sulfate and evaporated in vacuo. The residue was crystallized from isopropanol, yielding 6.2 gm (86% of theory) of N-(trans-3-chloroallyl)-noroxymorphone, which was found by thin-layer chromatography to be not completely pure. Recrystallization from 450 ml of toluene yielded 4.0 gm of the pure product having a melting point of 226° C. An additional 1 gm of the pure substance having the same melting point was obtained by concentrating the mother liquor to 50 ml.

The hydrochloride, m.p. 243° C., was obtained by dissolving the base in methanolic hydrochloric acid and adding ether to the solution until it just turned cloudy.

(b) 7.2 gm (0.02 mol) of N-trans-3-chloroallyl)-noroxymorphone were converted into O$^3$-acetyl-N-(trans-3-chloroallyl)-noroxymorphone by the procedure described in Example 9(a), yielding 9 gm of the O$^3$-acetylated derivative, which was dissolved in 50 ml of absolute methylene chloride and quaternized with 3.26 gm (0.022 mol) of trimethyloxomium fluoroborate in analogy to Example 10. The working up of the reaction mixture, accompanied by regeneration of the phenolic hydroxyl group and exchange of the fluoroborate anion for a bromide anion, was also effected in analogy to Example 10, yielding 1.2 gm of N-trans-3-chloroallyl)-noroxymorphone methobromide having a melting point of 200° C.

EXAMPLE 12

N-(Cis-3-chloroallyl)-noroxymorphone methobromide by method B (a) 6.48 gm (0.02 mol) of noroxymorphone hydrochloride were reacted with the 2.44 gm (0.022 mol) of cis-3-chloroallyl chloride in analogy to Example 11(a), the reaction mixture was evaporated, and the residue was taken up in a mixture of chloroform and water. The chloroform phase was separated and evaporated, and the residue was crystallized from 30 ml of toluene, yielding 6.1 gm (84.5% of theory) of N-(cis-3-chloroallyl)-noroxymorphone containing ¼ mol of toluene of crystallization; it first melted at 144° C. and then, after re-solidifying, again at 186° C. Its hydrochloride, m.p. 202° C., was obtained by dissolving the base in ethanolic hydrochloric acid and adding ether thereto until the solution just began to turn cloudy.

(b) 8.0 gm (0.0207 mol) of N-(cis-3-chloroallyl)-noroxymorphone with ¼ mol of toluene of crystallization were converted into the $O^3$-acetyl derivative, the latter was quaternized with trimethyloxonium fluoroborate, and the quaternary compound was converted into the methobromide, was described in Example 11 (b). 2.5 gm of N-(cis-3-chloroallyl)-noroxymorphone methobromide, m.p. 220° C., were obtained.

The compounds embraced by formula I above have useful pharmacodynamic properties. More particularly, they prevent or relieve the intestinal mobility inhibiting side-effect of narcotic analgesics, such as morphine and related opiates, meperidine, methadone or the like, in warm-blooded animals such as dogs, rats, and monkeys, without impairing the analgesic activity of the narcotic analgesic. In other words, the compounds of the present invention are useful for the prophylactic as well as therapeutic treatment of intestinal immobility associated with narcotic analgesics.

For pharmaceutical purposes the compounds of the present invention are administered to warm-blooded animals enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.133 mgm/kg to 1.33 mgm/kg body weight, depending upon the expected or existing severity of the intestinal mobility inhibition.

The following examples illustrate a few pharmaceutical dosage unit compositions comprising a compound of the present invention as an active ingredient and represent the best modes contemplated of using the invention. The parts are parts by weight unless otherwise specified.

EXAMPLE 13

Tablets

The tablet compositions is compounded from the following ingredients:

| | |
|---|---:|
| N-Allyl-noroxymorphone methobromide | 50 parts |
| Lactose | 95 parts |
| Corn starch | 45 parts |
| Colloidal silicic acid | 2 parts |
| Magnesium stearate | 3 parts |
| Soluble starch | 5 parts |
| Total | 200 parts |

Preparation

The active ingredient is intimately admixed with a portion of the inert excipients, and the mixture is granulated in conventional manner with the aid of an aqueous solution of the soluble starch. The granulate is then dried and admixed with the remainder of the inert excipients, and the composition is compressed into 200 mgm-tablets. Each table is an oral dosage unit composition containing 50 mgm of the active ingredient.

EXAMPLE 14

Coated pills

The pill core composition is compounded from the following ingredients:

| | |
|---|---:|
| N-Allyl-noroxymorphone methobromide | 75 parts |
| Lactose | 100 parts |
| Corn starch | 65 oarts |
| Colloidal silicic acid | 2 parts |
| Magnesium stearate | 3 parts |
| Soluble starch | 5 parts |
| Total | 250 parts |

Preparation

The ingredients are compounded as described in the preceding example, and the composition is compressed into 250-mgm-pill cores which are subsequently coated with a thin shell consisting essentially of a mixture of sugar, talcum and gum arabic, and polished with beeswax. Each coated pill is an oral dosage unit composition containing 75 mgm of the active ingredient.

EXAMPLE 15

Suppositories

The supporting composition is compounded from the following ingredients:

| | |
|---|---:|
| N-Allyl-noroxymorphone methoiodide | 50 parts |
| Lactose | 200 parts |
| Supporting base(e.g. coca butter) | 1450 parts |
| Total | 1700 parts |

Preparation

The active ingredient and the lactose are initimately admixed with each other, and the mixture is homogeneously blended into the molten supporting base. 1700 mgm-portions of the composition are poured into cooled supporting molds and allowed to harden therein. Each suppository is a rectal dosage unit composition containing 50 mgm of the active ingredient.

EXAMPLE 16

Hypodermic solution

The solution is compounded from the following ingredients:

| | |
|---|---|
| N-Allyl-noroxymorphone methobromide | 10 parts |
| Sodium chloride | 5 parts |
| Double-distilled water q.s.ad | 500 parts by volume |

Preparation

The active ingredient and the sodium chloride are dissolved in the distilled water, the solution is filtered until free from suspended particles, and the filtrate is filled into 5 cc-ampules which are sterilized and sealed. The contents of each ampules are an injectable dosage unit composition containing 10 mgm of the active ingredient.

EXAMPLE 17

Drop solution

The solution is compounded from the following ingredients:

| | |
|---|---|
| N-Allyl-noroxymorphone methochloride | 1.0 parts |
| Methyl p-hydroxy-benzoate | 0.07 parts |
| Propyl p-hydroxy-benzoate | 0.03 parts |
| De-mineralized water q.s.ad. | 100.00 parts by volume |

Preparation

The active ingredient and the p-hydroxy-benzoates (preservatives) are dissolved in the de-mineralized water, the solution is filtered, and the filtrate is filled into 100 ml-bottles. 5 ml of the solution are an oral dosage unit composition containing 50 mgm of the active ingredient.

Any one of the other compounds embraced by the formula I may be substituted for the particular quaternary noroxymorphone in Examples 13 through 17.

Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

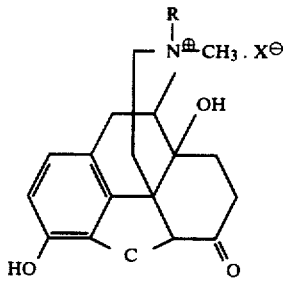

wherein

R is allyl, chloroallyl, cyclopropylmethyl or propargyl; and

X is a chloride, bromide, iodide, or methylsulfate anion.

2. The compound of claim 1, which is N-allylnoroxymorphone methobromide.

3. An intestinal immobility relieving pharmaceutical dosage unit composition consisting essentially of an inert pharmaceutical carrier and an effective intestinal immobility relieving amount of a compound of claim 1.

4. The method of preventing or relieving the intestinal mobility inhibiting side-effect of narcotic analgesics in a warm-blooded animal, which comprises administering to said animal an effective intestinal immobility relieving amount of a compound of claim 1.